US005112407A

United States Patent [19]

Sakai et al.

[11] Patent Number: 5,112,407

[45] Date of Patent: May 12, 1992

[54] PROCESS TO PREPARE MALTOSE POWDER

[75] Inventors: Shuzo Sakai; Hiroshi Akai; Toshio Miyake, all of Okayama, Japan

[73] Assignee: Kabushiki Kaisha Hayashibara Seibutsu Kagaku Kenkyujo, Okayama, Japan

[21] Appl. No.: 526,958

[22] Filed: May 22, 1990

Related U.S. Application Data

[63] Continuation of Ser. No. 195,002, May 17, 1988, abandoned.

[30] Foreign Application Priority Data

May 29, 1987 [JP] Japan ................................ 62-135697

[51] Int. Cl.[5] ........................ C12P 19/22; C07H 3/00; C13F 1/02

[52] U.S. Cl. ........................................ 127/58; 127/60; 435/95; 435/99; 536/124; 536/127

[58] Field of Search ............... 127/58, 60, 61; 435/95, 435/99; 536/100, 124, 127

[56] References Cited

U.S. PATENT DOCUMENTS

| | | | |
|---|---|---|---|
| 3,677,896 | 7/1972 | Kurimoto et al. | 435/95 |
| 3,795,584 | 3/1974 | Mitsuhashi et al. | 435/95 |
| 3,832,285 | 8/1974 | Kurimoto | 435/95 |
| 4,028,186 | 6/1977 | Sakai | 435/99 |
| 4,032,403 | 6/1977 | Sakai et al. | 435/95 |
| 4,487,198 | 12/1984 | Miyake et al. | 127/46.3 |
| 4,595,418 | 6/1986 | Yoshino | 127/60 |
| 4,870,059 | 9/1989 | Mitsuhashi et al. | 127/30 |

FOREIGN PATENT DOCUMENTS

| | | |
|---|---|---|
| 13089 | 4/1972 | Japan . |
| 3937 | 2/1979 | Japan . |
| 3938 | 2/1979 | Japan . |
| 17078 | 4/1981 | Japan . |
| 28153 | 6/1981 | Japan . |
| 28154 | 6/1981 | Japan . |
| 3356 | 1/1982 | Japan . |
| 92299 | 5/1985 | Japan . |
| 35800 | 3/1986 | Japan . |

OTHER PUBLICATIONS

Encyclopedia of Chemical Technology, Kirk-Othmer, 3rd Ed., vol. 21, "Maltose", p. 946, 1983.

*Primary Examiner*—Theodore Morris
*Assistant Examiner*—P. L. Hailey
*Attorney, Agent, or Firm*—Browdy and Neimark

[57] ABSTRACT

There is provided a process to prepare maltose powder containing crystalline beta-maltose hydrate, comprising concentrating an aqueous solution of a high-purity maltose having a maltose content of at least 85% DS to a moisture content below 10 w/w %, partially crystallizing alpha-maltose in the syrup, and crystallizing beta-maltose hydrate in the same syrup while converting the resultant crystalline alpha-maltose into crystalline beta-maltose hydrate. Use of the invention enables consistently high-quality maltose powders at a reduced drying cost.

3 Claims, No Drawings

PROCESS TO PREPARE MALTOSE POWDER

This application is a continuation of application Ser. No. 07/195,002, filed May 17, 1988, now abandoned.

BACKGROUND OF THE INVENTION

1. Field of the Invention

The present invention relates to a process to prepare maltose powder, specifically, to a process to prepare a stable maltose powder containing crystalline beta-maltose hydrate.

2. Description of the Prior Art

As disclosed, for example, in Japanese Patent Publication No. 3,937/79 and Japanese Patent Laid-Open No. 92,299/85, maltose powders containing crystalline beta-maltose hydrate have been manufactured by concentrating a high-purity maltose liquid to about 70–80 w/w % (moisture content of 20–30 w/w %), adding a seed crystal to the syrup, spray-drying a massecuite wherein crystallization of beta-maltose hydrate has proceeded to 30–50%, and ageing the resultant powder to a moisture content of 6 w/w %.

Conventional process, however, has the drawbacks that it consumes a relatively large amount of energy for drying at ambient temperature a maltose syrup having a relatively high moisture content (i.e. 20–30 w/w %) wherein crystallization of beta-maltose hydrate has been initiated by the addition of a seed crystal and this increases the manufacturing cost of maltose powder, as well as that a vigorous heating during the drying undesirably melts the resultant crystalline beta-maltose hydrate to hinder the attainment of a consistently high-quality maltose powder.

DETAILED DESCRIPTION OF THE INVENTION

In order to overcome these drawbacks of conventional process, the present inventors studied various conditions for crystallizing beta-maltose hydrate in a syrup having the possible highest concentration. As a result, the present inventors found that the crystallization rate at ambient temperature is not necessarily increased as the saturation degree in the syrup is elevated; as well as that the crystallization rate is maximized when the moisture content of the syrup is in the range of 20–30 w/w % and a moisture content out of this range retards the crystallization rate.

Also was found that crystallization of beta-maltose hydrate in a high-concentration syrup having a moisture content below 10 w/w %, specifically, about 5–8 w/w %, which is comparable to that of commercial maltose powder is not recommendable in industrial-scale preparation of maltose powder.

While, as disclosed in Japanese Patent Laid-Open No. 35,800/86, it has been known that a syrup having a moisture content below 10 w/w % tends to yield crystalline alpha-maltose.

By utilizing this, the present inventors discovered that the crystallization of beta-maltose hydrate is accelerable by partially crystallizing anhydrous alpha-maltose in a high-concentration syrup having a moisture content below 10 w/w %, preferably, about 5–8 w/w %, to increase the moisture content in its remaining amorphous part. Based on an additional finding that ageing of a crystalline alpha-maltose containing massecuite accelerates and facilitates both crystallization of beta-maltose hydrate and conversion of the crystalline alpha-maltose into crystalline beta-maltose hydrate, the present inventors established a novel process that enables industrial-scale preparation of a stable powder containing crystalline beta-maltose hydrate from a high-concentration syrup having a moisture content below 10 w/w %.

The wording "high-purity maltose" shall mean those having a maltose content of at least 80% DS (dry substance), preferably, 85% DS in order to obtain a satisfactorily stable maltose powder. To prepare such high-purity maltose from starch, a method as disclosed, for example, in Japanese Patent Publications Nos. 11,437/81 and 17,078/81, wherein gelatinized- or liquefied-starch is subjected to the action of beta-amylase and the released maltose is separated from polymer dextrins; and a method as disclosed, for example, in Japanese Patent Publications Nos. 13,089/72 and 3,938/79, wherein gelatinized- or liquefied-starch is subjected to beta-amylase and a starch debranching enzyme such as isoamylase and beta-amylase are employable.

The maltose content of the obtained high-purity maltose is augmentable by subjecting the contaminant saccharides, such as maltotriose, to an enzyme as disclosed, for example, in Japanese Patent Publications Nos. 28,153/81, 3,356/82 and 28,154/81, or by removing the contaminant saccharides with a fractionation as disclosed, for example, in Japanese Patent Laid-Open No. 23,799/83 using a column of strongly-acidic cation exchange resin. Such fractionation can be effected by the fixed bed-, moving bed- or simulated moving bed-method.

To concentrate an aqueous solution of the obtained high-purity maltose having a maltose content of at least 80% DS, preferably, 85% DS or higher, to a high-concentration syrup, desirably, the possible lowest cost procedure, for example, concentration in vacuo, is employed.

Such aqueous solution is prepared into a high-concentration syrup having a moisture content below 10 w/w %, preferably, about 5–8 w/w %, which is first kept at a temperature in the range of 50°–130° C. in the presence of a seed crystal to partially crystallize alpha-maltose, then aged at a temperature in the range of 10°–70° C. to crystallize beta-maltose hydrate while converting the resultant crystalline alpha-maltose into crystalline beta-maltose hydrate. The present inventors found that, when added to a syrup having a moisture content of 10 w/w % or higher, specifically, 12 w/w % or higher but lower than 25 w/w %, crystalline alpha-maltose dissolves in the syrup and substantially does not crystallize it, as well as that beta-maltose hydrate is much more crystallizable in such syrup.

Also was found that the presence of crystalline alpha-maltose in a high-concentration syrup having a moisture content below 5 w/w % is unfavorable because it requires addition of water to convert the crystalline alpha-maltose into crystalline beta-maltose hydrate.

An appropriate temperature for crystallizing alpha-maltose is 50°–130° C., preferably, 60°–120° C. An appropriate temperature for crystallizing beta-maltose hydrate and for converting crystalline alpha-maltose into crystalline beta-maltose hydrate is 10°–80° C., preferably, 20°–70° C.

Addition of a seed crystal is to accelerate the crystallization of maltose: Crystalline alpha-maltose, preferably, a mixture of crystalline alpha-maltose and crystalline beta-maltose hydrate is added as the seed crystal to a high-concentration syrup of a high-purity maltose in an amount of 0.001–20% DS, preferably, 0.1–5% DS, for example, by contacting, mixing and kneading.

To prepare the resultant syrup into a powder containing crystalline beta-maltose hydrate, for example, extrusion granulation and block pulverization are employable. In the case of the extrusion granulation, for example, while keeping at a temperature in the range of 60°–120° C., a high-concentration syrup of a high-purity maltose having a moisture content below 10 w/w % is kneaded together with a mixture of crystalline alpha-maltose and crystalline beta-maltose hydrate to effect a partial crystallization of alpha-maltose, and the resultant is fed to an extrusion granulator to obtain a granular massecuite or a granular powder which is then aged at a temperature in the range of 20°–70° C. to crystallize beta-maltose hydrate and also to convert the resultant crystalline alpha-maltose into crystalline beta-maltose hydrate.

Alternatively, such a high-concentration syrup is kneaded together with a crystalline alpha-maltose seed while keeping at a temperature in the range of 60°–120° C., and the resultant mixture is passed through an extrusion granulator while accelerating crystallization of alpha-maltose. The obtained granular massecuite is allowed to contact with a crystalline beta-maltose hydrate seed, and then aged at a temperature in the range of 20°–70° C. to accelerate both crystallization of beta-maltose hydrate and conversion of the resultant crystalline alpha-maltose into crystalline beta-maltose hydrate. Thus, a maltose powder containing crystalline beta-maltose hydrate is obtainable.

In the block pulverization, for example, a high-concentration syrup of a high-purity maltose having a moisture content below 10 w/w % is placed in a crystallizer, and mixed with a blend of crystalline alpha-maltose and crystalline beta-maltose hydrate while accelerating crystallization of alpha-maltose by keeping at a temperature in the range of 60°–120° C. The resultant massecuite is then transferred in a plastic tray, aged and solidified at a temperature in the range of 20°–70° C. The resultant block is cut and scraped with a cutting machine and/or a hammer mill to obtain a maltose powder containing crystalline beta-maltose hydrate. If necessary, moisture controlling, dehydrating and/or screening step can be provided before or after pulverizing step.

Since the obtained maltose powder having a moisture content approximately equal to that of the starting high-concentration syrup does require no or much less energy for postcrystallization drying, a consistently high-quality maltose powder can be manufactured at a reduced drying cost.

The mildly sweet white powder thus obtained is advantageously usable as a sweetener in various foods and beverages, as well as a humectant, vehicle or stabilizer in cosmetics, toiletries, pharmaceuticals and chemicals.

Several embodiments of the present invention will hereinafter be explained.

EXAMPLE 1

A liquefied starch solution having a DE (Dextrose Equivalent) of about 0.5 was prepared by adding to a suspension of 1 part by weight of potato starch in 10 parts by weight of water a commercial bacterial liquefying alpha-amylase (EC 3.2.1.1), heating the mixture to 90° C. to effect gelatinization, and further heating it quickly to 130° C. to suspend enzymatic reaction. To the solution was added 100 units/g starch of isoamylase (EC 3.2.1.68) prepared from a culture of *Pseudomonas amyloderamosa* ATCC 21262, and 50 units/g starch of "#1500", a beta-amylase (EC 3.2.1.2) derived from soybean, commercialized by Nagase & Company, Ltd., Osaka, Japan, and the resultant mixture was saccharified at pH 5.0 for 40 hours to obtain a high-purity maltose having a maltose content of 92.5% DS. The high-purity maltose was then purified by carbon decolorization and resin refining, and concentrated in vacuo to obtain a high-concentration syrup having a moisture content of 6.5 w/w %. The syrup was then placed in a kneader, and added with 1% DS crystalline alpha-maltose and 1% DS crystalline beta-maltose hydrate while keeping at 95° C. The resultant mixture was then kneaded for 3 minutes at this temperature, extruded in sheet shape, aged at 80° C. for 3 hours, further aged at 40° C. for 48 hours, and pulverized to obtain a maltose powder containing crystalline beta-maltose hydrate, moisture content of about 6.0 w/w %, in the yield of about 94% DS against the starting starch.

The product in a non-hygroscopic stable powder is advantageously usable as a sweetener having a perceived sweetness value of about ⅓ compared to sucrose in a variety of foods and beverages.

Furthermore, the product is advantageously usable as a humectant, vehicle or stabilizer in cosmetics, toiletries, pharmaceuticals and chemicals.

EXAMPLE 2

An aqueous solution of a high-purity maltose having a maltose content of 92.5% DS, obtained by the method in Example 1, was prepared into a high-concentration syrup having a moisture content of 5.8 w/w %. The syrup was then mixed with 2% DS crystalline alpha-maltose, and the mixture was granulated with an extrusion granulator. After ageing at 70° C. for 5 hours, the resultant granule was added with 2% DS crystalline beta-maltose, and the mixture was aged at 40° C. for 30 hours to obtain a maltose powder containing crystalline beta-maltose hydrate, moisture content of 5.3 w/w %, in the yield of about 95% DS against the starting starch.

Similarly as the product in Example 1, the product in a stable powder free of moisture uptake, and is advantageously usable in foods, beverages, cosmetics, toiletries and pharmaceuticals.

EXAMPLE 3

To a suspension of 2 parts by weight of corn starch in 10 parts by weight of water was added a commercial bacterial alpha-amylase, and the mixture was heated to 93° C. to effect liquefaction, followed by heating to 130° C. to suspend enzymatic reaction. The resultant liquefied starch solution having a DE of about 2 was quickly cooled to 55° C., and then added with isoamylase (EC 3.2.1.68) and a soybean beta-amylase in respective amount of 120 units/g starch and 100 units/g starch. The mixture was kept at pH 5.0 for 36 hours to effect saccharification, purified and concentrated similarly as in Example 1 to obtain a high-concentration syrup having a maltose content of about 88.2% DS and a moisture content of 6 w/w %. The syrup was then placed in a crystallizer, and added with 1% DS crystalline alpha-maltose seed and 1% DS crystalline beta-maltose hydrate seed at 90° C. After mixing for 5 minutes while keeping at this temperature, the resultant was transferred to plastic trays, and aged first at 70° C. for 10 hours then at 40° C. for 48 hours to obtain a massecuite solid in block shape. The massecuite solid was then cut and scraped with a pulverizer, and screened to obtain a maltose powder containing crystalline beta-maltose hydrate, moisture content of about 5.5 w/w %, in the yield of about 92% DS against the starting corn starch.

The massecuite solid was free of deformation and cracking, and exerted a satisfactory pulverizability.

Similarly as the product in Example 1, the product in a stable powder free of moisture uptake is advantageously usable in foods, beverages, cosmetics, toiletries and pharmaceuticals.

As described above, the present invention relates to a process to prepare a maltose powder containing crystalline beta-maltose hydrate from a high-concentration syrup having a moisture content below 10 w/w % which has been deemed hardly crystallizable. More particularly, the preparation of such maltose powder is facilitated by concentrating an aqueous solution of a high-purity maltose having a maltose content above 85 w/w % into a high-concentration syrup having a moisture content below 10 w/w %, crystallizing alpha-maltose in the presence of a crystalline alpha-maltose seed, and crystallizing beta-maltose hydrate while converting the resultant crystalline alpha-maltose into crystalline beta-maltose hydrate.

Since in the invention the postcrystallization drying can be carried out with no or much less amount of energy by concentrating in vacuo a high-concentration syrup to a moisture content approximately equal to a desired end product and this cuts a large amount energy for drying, consistently high-quality maltose powders are obtainable at a reduced drying cost. Thus, the present invention is very significant in the art.

The maltose powder obtained in this way is advantageously and extensively usable as a sweetener, humectant, vehicle or stabilizer in foods, beverages, cosmetics, toiletries, pharmaceuticals and chemicals.

While preferred embodiments has been described, variations thereto will occur to those skilled in the art within the scope of the present inventive concepts which are delineated by the following claims.

We claim:

1. A process for preparing crystalline β-maltose hydrate consisting essentially of:

(a) concentrating an aqueous solution of a highpurity maltose having a maltose content of at least 85% by weight, on a dry solids basis, to a moisture content below 10% by weight;

(b) crystallizing α-maltose in the resultant highconcentration syrup to increase the moisture content in the amorphous part of the syrup while maintaining the syrup at a temperature in the range of 60°–120° C. in the presence of crystalline α-maltose seed or a mixture of crystalline α-maltose seed with crystalline β-maltose hydrate;

(c) converting said crystalline α-maltose in the resultant mixture to β-maltose hydrate while maintaining the mixture at a temperature below the temperature used in (b) in the range of 20–70° C.; and (d) pulverizing the mixture mainly composed of crystalline β-maltose hydrate.

2. The process according to claim 1 wherein said high-concentration syrup has a moisture content in the range of 5.0 to 8.0% by weight.

3. A process for preparing cyrstalline β-maltose hydrate consisting of:

(a) concentrating an aqueous solution of a high-purity maltose having a maltose content of at least 85% by weight, on a dry solids basis, to provide a high-concentration syrup having a moisture content below 10% by weight;

(b) crystallizing α-maltose in the resultant high-concentration syrup to increase the moisture content in an amorphous part of the syrup while maintaining the syrup at a temperature in the range of 60°–120° C., said crystallizing being carried out in the presence of crystalline α-maltose seed or a mixture of crystalline α-maltose seed with crystalline β-maltose hydrate;

(c) converting said crystalline α-maltose in the resultant mixture to β-maltose hydrate while maintaining the mixture at 20°–70° C.; and (d) pulverizing the mixture mainly composed of crystalline β-maltose hydrate.

* * * * *